(12) United States Patent
Clarke et al.

(10) Patent No.: US 7,625,427 B2
(45) Date of Patent: Dec. 1, 2009

(54) APPARATUS AND PROCESS FOR CARBON DIOXIDE ABSORPTION

(75) Inventors: Michael John Clarke, Essex (GB); Ian Hallas, Sheffield (GB)

(73) Assignee: Molecular Products Limited, Essex (GB)

( * ) Notice: Subject to any disclaimer, the term of this patent is extended or adjusted under 35 U.S.C. 154(b) by 348 days.

(21) Appl. No.: 10/536,659

(22) PCT Filed: Dec. 1, 2003

(86) PCT No.: PCT/GB03/05226

§ 371 (c)(1),
(2), (4) Date: Nov. 23, 2005

(87) PCT Pub. No.: WO2004/050154

PCT Pub. Date: Jun. 17, 2004

(65) Prior Publication Data

US 2006/0144235 A1    Jul. 6, 2006

(30) Foreign Application Priority Data

Dec. 2, 2002   (GB) ................................ 0228074.1

(51) Int. Cl.
*B01D 53/22*   (2006.01)
*A61M 16/01*   (2006.01)

(52) U.S. Cl. ............... 95/51; 95/44; 96/5; 96/8; 96/10; 96/11; 128/205.28

(58) Field of Classification Search ............... 95/44, 95/51, 54; 96/5, 8, 10, 11; 128/205.28
See application file for complete search history.

(56) References Cited

U.S. PATENT DOCUMENTS

| | | | |
|---|---|---|---|
| 3,674,022 A | 7/1972 | Dounoucos | 7/2 |
| 4,174,374 A | 11/1979 | Matson | 53/34 |
| 4,750,918 A * | 6/1988 | Sirkar | 95/44 |
| 4,824,443 A | 4/1989 | Matson et al. | 53/22 |
| 4,928,683 A * | 5/1990 | Westerkamp et al. | 128/203.12 |
| 5,281,254 A * | 1/1994 | Birbara et al. | 95/44 |
| 5,445,669 A * | 8/1995 | Nakabayashi et al. | 96/5 |
| 5,749,941 A * | 5/1998 | Jansen et al. | 95/44 |
| 5,876,486 A * | 3/1999 | Steinwandel et al. | 95/44 |
| 6,156,096 A * | 12/2000 | Sirkar | 95/44 |
| 6,635,103 B2 * | 10/2003 | Sirkar et al. | 95/44 |
| 2004/0053782 A1* | 3/2004 | Holder | 502/400 |
| 2008/0060651 A1* | 3/2008 | Riecke | 128/205.28 |

FOREIGN PATENT DOCUMENTS

| | | | |
|---|---|---|---|
| DE | 19645223 C1 | 11/1996 | |
| DE | 19729739 A1 | 7/1997 | |
| EP | 0201468 | 4/1986 | 53/34 |
| GB | 1517362 | 8/1975 | |
| WO | WO9401204 | 7/1993 | |

OTHER PUBLICATIONS

Facilitated Transport of Carbon Dioxide through Supported Liquid Membranes of Aqueous Amine Solutions. *1996 American Chemical Society. Ind. Eng. Chem. Res.* Vo. 35, No. 2, p. 538-545. by Teramota, Nakai, Ohnishi, Huang, Watari and Matsuyama.
*Supported Liquid Membranes For Carbon Dioxide Removal From Submarine Atmospheres: Experiences with a technology demonstrator.* 2001-01-2394 By Gareth Toft, Steve Cassidy and Mark Lunn. Defense Evaluation and Research Agency on behalf of the Controller of HMSO.

* cited by examiner

*Primary Examiner*—Jason M Greene
(74) *Attorney, Agent, or Firm*—Stout, Uxa, Buyan & Mullins; Frank J. Uxa

(57) ABSTRACT

Carbon dioxide is separated from a gas stream using a supported carrier liquid membrane having a selected concentration of carrier species, the method being especially suitable for use in anaesthesia under conditions of periodic flow.

22 Claims, No Drawings

APPARATUS AND PROCESS FOR CARBON DIOXIDE ABSORPTION

This invention relates to a method, apparatus and device for absorbing carbon dioxide from a feedstream, especially a gaseous feedstream, more especially an air stream.

Carbon dioxide absorption is important in many fields, especially where a person's exhaled breath is being recycled as in certain types of underwater and emergency rescue operations and, especially, anaesthesia, more especially low flow and closed circuit anaesthesia. Chemical absorption is frequently employed, generally using sodalime or, more recently, enhanced formulations based on sodalime, e.g., one using calcium or magnesium chloride to increase sodalime's absorption capacity, or using an alkali metal-free formulation, e.g., one based on calcium hydroxide and calcium chloride. Formulations free from alkali metal hydroxides have an advantage in anaesthesia in that they have a lower tendency to produce toxic volatile degradation products when fluorinate anaesthetics, for example sevoflurane and desflurane, are used.

However, absorbent chemical formulations of such types require frequent replacement, and environmentally acceptable disposal of used materials is becoming increasingly difficult.

There accordingly remains a need for a means to absorb carbon dioxide ($CO_2$) that has a longer useful life. That need must be met, however, without losing from the gas stream and, especially, discharging to the atmosphere too great a proportion of those components of the gas stream that it is desired to retain.

There accordingly also remains a need for a means of separating $CO_2$ from an anaesthetic gas-containing or similar gas stream in which the separation factor is at an acceptable level.

In this specification, the separation factor, $\alpha$, is given by $$\alpha(CO_2, a) = \frac{R_{CO2}}{p_{CO2}} \cdot \frac{p_a}{R_a}$$

wherein R represents permeation rate, p partial pressure of a gas in the feed gas stream and a an anaesthetic or other gas or gases that it is desired to retain in the feed gas stream.

There further remains a need for a means of separating $CO_2$ from a gas stream in which variations in flow rate occur, especially the periodic flow rate variation in the gas stream from a subject under mechanical ventilation as in, for example, anaesthesia. Flow other than constant flow reduces the contact time available for reaction at the absorber surface at certain periods in a cycle. If the gas transfer rate is insufficient, incomplete absorption may result unless membrane area is increased.

The present invention is based on the observation that a supported liquid membrane having certain characteristics removes $CO_2$ from a gas stream also containing an anaesthetic at an acceptable separation factor. This has been found to be the case even when the gas stream is one in which substantial variations occur periodically in the flow rate.

The separation of $CO_2$ from a gas mixture using a supported liquid membrane has previously been described, for example by Teramoto et al, Ind. Eng. Chem. Res. 1996, 35, 538. The membrane comprised a microporous polymer support layer and a liquid membrane phase retained in the pores of the polymer; the polymer used was poly(vinylidene fluoride) and the liquid carrier was an aqueous solution of monoethanolamine or diethanolamine.

It has been found, however, that the separation factor, or membrane selectivity, of the supported liquid membranes reported by Teramoto to be good in a $CO_2/CH_4$ system is not entirely satisfactory in a mixture of $CO_2$ in certain other gases. This appears to be because the permeation rate of other gases, for example, $N_2O$, which should remain in the gas mixture retentate, is such that unacceptable losses through the membrane occur. Special difficulties arise when the stream is a certain type of low flow or closed circuit anaesthetic stream.

Tests have shown that the method, apparatus, and device, of the invention are effective in separating $CO_2$ from a feed gas stream varying in pressure, particularly sinusoidally, as occurs in, for example, low flow or closed circuit anaesthesia, while retaining anaesthetics, e.g., $N_2O$ and sevoflurane, to a satisfactory degree.

The invention provides apparatus for separating $CO_2$ from a gas stream containing $CO_2$ and an anaesthetic gas, the apparatus comprising a gas separation device and means for transporting the gas stream at a periodically varying flow rate through the gas separation device, the device comprising a supported carrier liquid membrane in which the carrier species is an organic base present at a concentration sufficient to provide a separation factor $\alpha$ ($CO_2$, a), where $\alpha$ and a have the meanings defined above, greater than unity.

Advantageously the concentration is such as to provide an $\alpha$ of at least 10, preferably at least 15, more preferably at least 60, and most preferably at least 120.

One form of device capable of giving the desired separation factor, and accordingly also provided by the invention, is a device for separating gases which comprises a supported carrier liquid membrane in which the carrier species is an organic base present in a concentration of at least 4.5 mol.$dm^{-3}$, advantageously within the range of 4.5 to 6 mol.$dm^{-3}$, of liquid. The invention also provides apparatus as set out above comprising such a device.

The present invention also provides a method for the separation of carbon dioxide from a gas stream containing it, which comprises contacting the gas stream with a supported carrier liquid membrane in which the carrier species is an organic base present in a concentration of at least 4.5 mol.$dm^{-3}$, advantageously within the range of from 4.5 to 6 mol.$dm^{-3}$, of liquid.

The invention also provides a method of separating carbon dioxide from a gas stream in anaesthesia, especially low flow or closed circuit anaesthesia, which comprises contacting a gas stream containing carbon dioxide with a supported carrier liquid membrane in which the carrier is an organic base present at a concentration sufficient to provide a separation factor $\alpha$ ($CO_2$, a) as set out above. The invention further provides such a method in which the carrier is present in a concentration of at least 4.5 mol.$dm^{-3}$ and advantageously within the range of from 4.5 to 6 mol.$dm^{-3}$.

The gas stream advantageously passes the membrane at a periodically, e.g., sinusoidally, varying flow rate.

The means for transporting the gas stream at a periodically varying flow rate may be a bellows ventilator, advantageously an air-driven, microprocessor-controlled, ventilator.

The invention further provides apparatus and a device as set out above, which also comprises means for generating a sweep gas stream, and means for humidifying the sweep stream.

Advantageously the carrier species is one capable of reacting reversibly with $CO_2$ and is soluble in or miscible with a selected solvent. The organic base carrier species is advantageously an aliphatic base, for example a monoamine, or especially a polyamine or an alkanolamine, for example a mono-, di-, or tri-ethanolamine, diisopropanolamine, ethylenediamine, or a salt of glycine, e.g., the sodium salt. Advantageously, the solvent is one containing at least one hydroxyl group, for example one or more of glycerol, polyethylene glycol or, preferably, water. Other organic solvents, optionally in admixture with water, may be used.

The porous membrane support may be of, for example, polypropylene, polycarbonate, poly(vinylidene fluoride), polysulphone or polyacrylonitrile. Advantageously the support is as thin as possible, consistent with a sufficient mechanical strength, and has high porosity but low pore tortuosity. When the solvent is water, the support is advantageously hydrophilic.

The membrane support may be in sheet form, for example in a spirally wound or folded sheet configuration or, preferably, in the form of hollow fibres. The fibres may typically be in the form of a bundle, which may be supported or, preferably, unsupported along its length. In order to maximize contact of gas with the fibre surfaces, the fibre packing density is as low as possible consistent with an economic size of the device. Further, in a device employing a plurality of fibre bundles, the bundles have as small a diameter as possible, and are spaced as far apart as possible, again consistent with an economic device size.

It has been found preferable for the feed stream to be within the fibres and the sweep gas to be on the shell side, this configuration enabling higher sweep gas rates to be used, maximizing $CO_2$ removal rates.

When a plurality of similar membrane assemblies, e.g., fibre bundles, is employed, advantageously the gas stream is divided evenly among them. Advantageously, therefore, plenum chambers are provided upstream and downstream of the membrane assemblies, enabling the gas stream to be divided and recombined.

The method of the invention may employ a vacuum on the face of the membrane remote from the gas stream; advantageously, however, a sweep gas is used to assist in transporting the permeate from the membrane surface. The sweep gas may be, for example, ambient air, advantageously maintained at a high relative humidity. In medical and surgical uses, the air may be the supply of "medical air" normally available in hospital operating theatres, which is typically at a pressure sufficient to overcome the device resistance and the associated pressure drop. This air is, however, typically at low relative humidity, and necessitates a greater humidification capacity. When vacuum sweep is employed, lower humidification capacity but a greater capacity of vacuum plant are required.

The relative humidity of the sweep stream is advantageously maintained at a high level, preferably as close to saturation as possible, to avoid undesirable changes in the composition of the liquid membrane. Allowing or causing the carrier liquid concentration to rise above a desired level, by evaporation of solvent, especially water, may cause reduced gas transfer through the membrane by an undesirably high membrane viscosity.

Similarly, if desired or required, the feed gas stream may be humidified, by any suitable means.

The sweep gas is desirably maintained at a desired high relative humidity by, for example, delivering a metered water supply to the sweep gas stream, by a water spray or by an ultrasonic humidifier. In certain environments, condensation and recycling of moisture in the exiting sweep stream may be desirable, if health considerations permit.

Advantageously, the assembly comprises a single membrane-containing unit or a plurality of such units, especially hollow fibre membrane-containing units. Each unit advantageously contains a plurality of hollow fibres. The total surface area of the assembly is sufficient to remove enough $CO_2$ from an anaesthetic circuit to support life, and is advantageously in the range of 5 to 25 $m^3$. The surface area required may be minimized by maximizing the contact efficiency. This may be achieved, for example, by including baffles in the shell of the assembly or by use of structured fibre packing.

The means for generating the sweep stream may be, if the stream is air, a fan or compressor capable of delivering from 7.5 to 45 liters $min^{-1}$ $m^{-2}$, especially about 30 liters $min^{-1}$ $m^{-2}$, of membrane area, especially about 600 l $min^{-1}$, through the assembly. If the sweep is a vacuum sweep, the means may be, for example, a pump capable of maintaining the shell at a pressure of at most 4 mm Hg, preferably at most 0.8 mm Hg.

As indicated above, the means for humidifying the sweep stream may be, for example, a water spray or an ultrasonic humidifier.

In an alternative embodiment, a mass of carrier liquid, for example, the aqueous solution of the organic base, and a second membrane are interposed between the gas stream and the sweep stream. In this embodiment, there are advantageously provided two units, each comprising, for example, a bundle of hollow fibre membranes, the gas stream passing through the interior of the fibres in one unit and the sweep stream passing through the interior of the fibres in the other, the carrier liquid contacting the exterior of the fibres in each unit and being circulated between them. Any loss of solvent, e.g., water, to the sweep stream from the membrane in the second unit is compensated by transfer from the mass of carrier liquid, which in turn may be continuously or periodically replenished. The sweep stream, e.g., the sweep gas, need not then be humidified.

The following example illustrates the invention:

Tests were carried out on membrane units with polyacrylonitrile fibres, surface area about 1.3 $m^2$ (Pan-SF 650, Asahi Medical), the fibres containing aqueous diethanolamine (DEA) solutions of various concentrations. A circuit was set up using a feed gas stream containing 23% oxygen, 77% nitrous oxide, by volume into which was fed 3% carbon dioxide, and a sweep gas stream of humidified air, all at ambient temperature. The feed gas stream was applied at a sinusoidal flow rate variation as used in mechanical ventilation of a patient under anaesthetic, at a mean flow rate of 1 litre $min^{-1}$, using an Aestiva 3000 unit, made by Datex-Ohmeda.

The permeation rates of $CO_2$ and $N_2O$ through the membranes were measured after the concentrations of gases reached a steady state, and the results are shown in Table 1. The $CO_2$ concentration rate shown is an average of the "inspired" and "expired" concentrations.

TABLE 1

| DEA Concentration mol.$dm^{-3}$ | $CO_2$ | | $N_2O$ | | |
| --- | --- | --- | --- | --- | --- |
| | Conc. vol % | Permeation rate ml.$min^{-1}$ | Conc. vol % | Permeation rate ml.$min^{-1}$ | α |
| 2 | 1.75 | 39.86 | 28 | 109.44 | 5.83 |
| 4 | 1.7 | 39.87 | 37 | 100.66 | 8.62 |
| 4.5 | 1.8 | 39.73 | 58 | 73.21 | 17.49 |
| 5 | 2.0 | 39.55 | 58 | 73.21 | 15.67 |
| 5.5 | 1.9 | 39.62 | 62 | 65.38 | 19.77 |
| 6 | 2.4 | 39.13 | 61 | 66.35 | 14.99 |
| 6.5 | 4.2 | 36.15 | 62 | 60.42 | 8.83 |
| 7 | 11.2 | 27.88 | 62 | 47.50 | 3.25 |

α, the separation factor or membrane selectivity, is given by:
$$\alpha = \frac{\text{permeation rate } CO_2}{\text{partial pressure } CO_2} \times \frac{\text{partial pressure } N_2O}{\text{permeation rate } N_2O}$$

The final column of the table shows clearly the substantial proportional increase in desired separation of $CO_2$ over unwanted loss of $N_2O$ between 4 and 4.5 mol.$dm^{-1}$ concentrations, this being maintained almost to the highest concentration tested. The example above shows that the carrier species at the concentrations used readily gives an α of from 15 to 20 under the test conditions. However, as can be seen from the second column of the table, the $CO_2$ permeation rate and α value begin to fall when the concentration exceeds about 6 mol.$dm^{-3}$.

It is believed that an optimum concentration is equivalent to that in which the amine is substantially fully hydrated with little or no greater proportion of solvent e.g., water.

The invention claimed is:

1. A method of separating $CO_2$ from a gas stream containing $CO_2$ and an anaesthetic gas, which comprises transporting the gas stream at a periodically varying flow rate through a gas separation device, said device comprising a supported carrier liquid membrane in which the carrier species is an organic base present at a concentration sufficient to provide a separation factor α ($CO_2$, a), $$\text{where } \alpha(CO_2, a) = \frac{R_{CO2}}{p_{CO2}} \cdot \frac{p_a}{R_a}$$

wherein R represents permeation rate, p partial pressure of a gas in the feed gas stream and a an anaesthetic gas, greater than unity.

2. A method for separating gases in a gas stream, which comprises contacting the gas stream comprising carbon dioxide and an anaesthetic gas with a supported carrier liquid membrane in which the carrier is an organic base present in a concentration of at least 4.5 mol.$dm^{-3}$.

3. A method, as claimed in claim 2, in which the gas stream is transported at a periodically varying flow rate over the supported carrier liquid membrane.

4. A method as claimed in claim 1, wherein the device comprises a supported carrier liquid membrane in which the carrier species is present in a concentration of at least 4.5 mol.$dm^{-3}$.

5. A method as claimed in claim 1, wherein the membrane is a hollow fibre membrane, and is in the form of a fibre bundle.

6. A method as claimed in claim 1, which further comprises generating a sweep gas stream or providing a vacuum on a face of the membrane remote from the gas stream.

7. A method as claimed in claim 6, which further comprises humidifying the sweep gas stream.

8. A method as claimed in claim 2, wherein the membrane is a hollow fibre membrane, and is in the form of a fibre bundle.

9. A method as claimed in claim 2, which further comprises generating a sweep gas stream or providing a vacuum on a face of the membrane remote from the gas stream.

10. A method as claimed in claim 9, which further comprises humidifying the sweep gas stream.

11. Apparatus for separating $CO_2$ from a gas stream containing $CO_2$ and an anaesthetic gas, the apparatus comprising a gas separation device and means comprising a bellows ventilator for transporting the gas stream at a sinusoidally varying flow rate through the gas separation device, the device comprising a supported carrier liquid membrane in which the carrier species is an organic base present at a concentration sufficient to provide a separation factor α ($CO_2$, a), $$\text{where } \alpha(CO_2, a) = \frac{R_{CO2}}{p_{CO2}} \cdot \frac{p_a}{R_a}$$

wherein R represents permeation rate, p partial pressure of a gas in the feed gas stream and a an anaesthetic gas, greater than unity.

12. Apparatus as claimed in claim 11, wherein the device comprises a supported carrier liquid membrane in which the carrier is present in a concentration of at least 4.5 mol.$dm^{-3}$.

13. Apparatus as claimed in claim 11, wherein the membrane is a hollow fibre membrane, and is in the form of a fibre bundle.

14. Apparatus as claimed in claim 11, which further comprises means for generating a sweep gas stream or means for providing a vacuum on a face of the membrane remote from the gas stream.

15. Apparatus as claimed in claim 14, which further comprises means for humidifying the sweep gas stream.

16. A method as claimed in claim 1, wherein the organic base is selected from the group consisting of diethanolamine, ethanolamine and ethylenediamine.

17. Apparatus as claimed in claim 11, wherein the organic base is selected from the group consisting of diethanolamine, ethanolamine and ethylenediamine.

18. Apparatus for separating $CO_2$ from a gas stream containing $CO_2$ and an anaesthetic gas, the apparatus comprising a gas separation device and a means for transporting the gas stream at a sinusoidally varying flow rate through the gas separation device, the means comprising a bellows ventilator, the device comprising a supported carrier liquid membrane in which the carrier is an organic base present in a concentration of at least 4.5 mol.$dm^{-3}$.

19. Apparatus as claimed in claim 18, wherein the membrane is a hollow fibre membrane, and is in the form of a fibre bundle.

20. Apparatus as claimed in claim 18, which further comprises means for generating a sweep gas stream or means for providing a vacuum on a face of the membrane remote from the gas stream.

21. Apparatus as claimed in claim 20, which further comprises means for humidifying the sweep gas stream.

22. Apparatus as claimed in claim 18, wherein the organic base is selected from the group consisting of diethanolamine, ethanolamine and ethylenediamine.

* * * * *

UNITED STATES PATENT AND TRADEMARK OFFICE
CERTIFICATE OF CORRECTION

| | |
|---|---|
| PATENT NO. | : 7,625,427 B2 |
| APPLICATION NO. | : 10/536659 |
| DATED | : December 1, 2009 |
| INVENTOR(S) | : Clarke et al. |

It is certified that error appears in the above-identified patent and that said Letters Patent is hereby corrected as shown below:

Title Page
(*) Notice    Delete the phrase "by 348 days" and insert --by 739 days--.

Column 5, line 31
In claim 3, delete the "," after "A method".

Signed and Sealed this

Twenty-fourth Day of August, 2010

David J. Kappos
*Director of the United States Patent and Trademark Office*